(12) United States Patent
Hamas

(10) Patent No.: US 6,802,861 B1
(45) Date of Patent: Oct. 12, 2004

(54) STRUCTURED BREAST IMPLANT

(75) Inventor: Robert S. Hamas, Dallas, TX (US)

(73) Assignee: RSH-GS Trust, Dallas, TX (US)

( * ) Notice: Subject to any disclaimer, the term of this patent is extended or adjusted under 35 U.S.C. 154(b) by 0 days.

(21) Appl. No.: 10/649,558

(22) Filed: Aug. 26, 2003

(51) Int. Cl.$^7$ .................................................. A61F 2/52
(52) U.S. Cl. ............................................. 623/7; 623/8
(58) Field of Search .......................................... 623/7–8

(56) References Cited

U.S. PATENT DOCUMENTS

| | | | | |
|---|---|---|---|---|
| 4,298,998 A | * | 11/1981 | Naficy | 623/8 |
| 4,531,244 A | | 7/1985 | Hamas | |
| 4,773,909 A | * | 9/1988 | Chaglassian | 623/8 |
| 4,944,750 A | * | 7/1990 | Cox, Jr. | 623/8 |
| 5,358,521 A | * | 10/1994 | Shane | 623/8 |
| 5,496,367 A | | 3/1996 | Fisher | |
| 5,496,370 A | | 3/1996 | Hamas | |
| 6,113,634 A | * | 9/2000 | Weber-Unger et al. | 623/7 |
| 6,146,418 A | * | 11/2000 | Berman | 623/8 |
| 6,183,514 B1 | * | 2/2001 | Becker | 623/8 |
| 6,638,308 B2 | * | 10/2003 | Corbitt et al. | 623/8 |
| 6,666,893 B2 | * | 12/2003 | Burg et al. | 623/23.75 |
| 2003/0144734 A1 | * | 7/2003 | Dreschnack et al. | 623/8 |
| 2003/0163197 A1 | * | 8/2003 | Chen | 623/7 |

* cited by examiner

*Primary Examiner*—Suzette J. Jackson
(74) *Attorney, Agent, or Firm*—Webb Ziesenheim Logsdon Orkin & Hanson, P.C.

(57) ABSTRACT

A surgically implantable prosthetic device includes a first shell having an exterior surface, an interior surface, and enclosing a lumen, wherein the lumen enclosed by the first shell is able to accommodate a first fluid therein. The prosthetic device further includes a second shell having an exterior surface, an interior surface, and enclosing a lumen, wherein the lumen enclosed by the second shell is able to accommodate a second fluid therein. One or more fitted shells arranged adjacent to and in a graduated relation to each other are situated between the exterior surface of the second shell and the interior surface of the first shell. The one or more shells include an innermost fitted shell and an outermost fitted shell, wherein the innermost fitted shell is adjacent to the exterior surface of the second shell and the outermost fitted shell is adjacent to the interior surface of the first shell.

20 Claims, 2 Drawing Sheets

STRUCTURED BREAST IMPLANT

BACKGROUND OF THE INVENTION

1. Field of the Invention

This invention relates generally to surgically implantable prosthetic devices and, more specifically, to mammary prostheses.

2. Description of Related Art

It has become a practice in the field of surgery to place a prosthetic implant in various areas of the body under any one of various conditions. In cases where cancerous, precancerous, or other abnormal or damaged tissue has been removed, the prosthetic implant is often used as a replacement for the removed tissue and its purpose is to retain the original body contour. An implant of this character provides physical support for the surrounding body tissue, and by filling any voids that are created by the removal of the body tissue preserves the normal outward appearance and feel of the body. Prosthetic devices have also been used to enhance or augment the appearance of body parts.

Breast prostheses have long been used for breast augmentation and for reconstructive surgery following a mastectomy. The prostheses are available in numerous sizes and shapes including teardrop, round, low profile, and high profile. Usually, breast prostheses are implanted via a small inframammary or peri-aerolar incision into a pocket dissected deep to the patient's own breast tissue in front of the pectoral muscle. In certain situations, the prosthesis may be placed behind the various chest muscles.

Some prosthetic devices have utilized an outer shell or envelope which is filled with a silicone gel, a saline solution, or other liquid, such as an oil or polymer. Other breast prosthetic devices have utilized an envelope which is filled with a combination of silicone gel and saline solution in separate compartments. Prior art silicone gel devices have tactile properties similar to normal tissue, but suffer from certain disadvantages. First, some silicone may bleed through the envelope and migrate into the tissue. Second, rupture of the envelope of a silicone gel implant is difficult for a patient to detect. Third, silicone gel from a ruptured implant may cause an undesirable tissue response.

Some breast prosthetic devices have utilized an outer shell or envelope which is filled with a saline solution. The prior art saline solution filled prosthetic devices suffer from certain disadvantages and lack the proper appearance and tactile properties due to several factors. First, the saline solution displaces too quickly to give the proper tactile properties. Second, the ease of displacement of the saline solution can create a "fluid wave" in the implant presenting an unnatural look of the prosthetic device. Third, when the saline solution displaces from one area of the implant, the lack of volume in that area may result in visible wrinkling of the envelope. Fourth, the outer shell or envelope can fold upon itself, causing an area of wear (e.g., fold flaw), leading to failure and deflation.

There are breast prosthetic devices utilizing an outer envelope, wherein the envelope contains baffle forming material. The baffle forming material fills at least a portion of the outer envelope, while the remainder of the outer envelope is filled with a fluid, such as saline solution. The baffle forming material may or may not be attached to the outer envelope. The drawback to such prior art baffle forming material is that such material does not match the single layer structure, geometry, proportions, etc., of the outer envelope, thereby resulting in wrinkling and folding of the implant due to the uncontrolled position of the baffle forming material. Additionally, some of the prior art baffle material can be felt through the implant, resulting in an unnatural feel to the implant.

The object of the present invention is to overcome some of the drawbacks of the prior art implants. It is desirable to construct a surgically implantable prosthetic device which may be filled with saline and/or other fluids and which has the appropriate tactile feel, appearance, and other characteristics found in a human breast. Specifically, the present invention controls the position of the baffle forming material within the lumen with either minimum or no attachment points.

SUMMARY OF THE INVENTION

Briefly, according to the present invention, there is provided a surgically implantable prosthetic device, comprising an outer shell having an exterior surface, an interior surface, and enclosing an outer lumen or cavity, wherein the outer lumen is able to accommodate a first fluid therein. The prosthetic device further comprises an inner shell having an exterior surface, an interior surface, and enclosing an inner lumen or cavity, wherein the inner lumen is able to accommodate a second fluid therein. Additionally, the prosthetic device has one or more fitted shells situated between the exterior surface of the inner shell and the interior surface of the outer shell. The fitted shells are adjacent to each other and are arranged in a graduated manner, more specifically, a smaller shell is contained within a successive larger shell.

Both the outer lumen of the outer shell and the inner lumen of the inner shell may be filled with a fluid. The fluid is able to move within the outer lumen and envelop the fitted shells. A saline solution would be an appropriate choice for use as the fluid. Saline refers to any electrolyte combination together with water, however, the invention is not limited solely to the use of saline. Other fluids may be utilized such as, for example, organic polymers or protein fluids; furthermore, certain gases may possibly be utilized as substitutes for fluids. Lubricating agents may be added to the saline.

The prosthetic device utilizing saline or the like provides a safe and harmless prosthetic implant. If the outer shell is ruptured or compromised in any fashion, the saline is safely absorbed into the body tissue. Furthermore, the patient would observe the decrease in volume of the implant and quickly come in for a replacement. This quick indication of implant failure decreases the chance that there would be time for tissue to grow into the implant material after implant rupture due to lack of discovery.

The outer lumen and/or the inner lumen may be pre-filled prior to implantation or, alternatively, may be first implanted and then filled with the fluid. One or more valves may be provided for the filling of the outer lumen, which includes the spaces between the fitted shells, and the inner lumen.

The arrangement of the lumens, the fitted shells, and the inner and outer shells decreases the displacement rate of the fluid. This restriction of the ability of the fluid to move inside the outer lumen improves the desired tactile characteristics of the implant and reduces the "fluid wave" effect of the implant. Furthermore, this fitted shell arrangement prevents wrinkling, folding, or bunching together of the baffle material within the implant. Additionally, the outer shell is supported, feels smooth externally, and does not fold upon itself to create wear points.

These and other advantages of the present invention will be understood from the description of the desirable embodiments, taken with the accompanying drawings, wherein like reference numerals represent like elements throughout.

DESCRIPTION OF THE PREFERRED EMBODIMENTS

Figure 1:
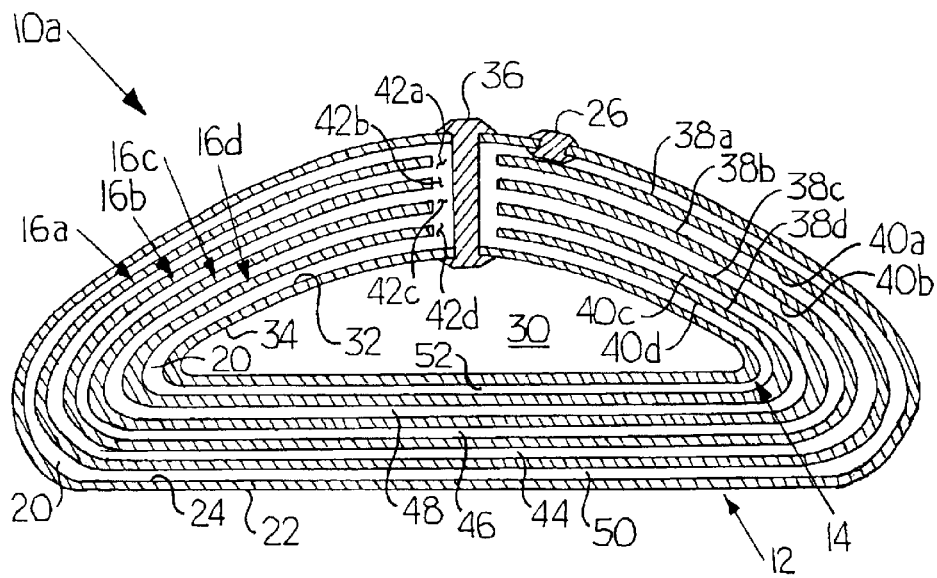
FIG. 1 is a cross-sectional side view of an implant, in accordance with the present invention.

For purposes of the description hereinafter, the spatial or directional terms, such as "inner", "outer", "top", "bottom", "central", and derivatives thereof, shall relate to the invention as it is oriented in the drawing figures. However, it is to be understood that the invention may assume various alternative variations, except where expressly specified to the contrary. It is also to be understood that the specific apparatus illustrated in the attached drawings and described in the following specification is simply an exemplary embodiment of the present invention. Hence, specific dimensions and other physical characteristics related to the embodiments disclosed herein are not to be considered as limiting.

Implant 10a, a first alternative embodiment implant 10b, a second alternative embodiment implant 10c, and a third alternative embodiment implant 10d, according to the present invention, are illustrated in FIGS. 1–4. The implant 10a is particularly adapted for use as a surgically implantable mammary prosthesis. The implant 10a includes an outer shell 12 enclosing a lumen or a cavity, an inner shell 14 enclosing a lumen or a cavity, and one or more generally dome-shaped fitted shells, e.g., a first fitted shell 16a, a second fitted shell 16b, a third fitted shell 16c, and a fourth fitted shell 16d. In a particularly desirable embodiment, with reference to the implant 10a as it is oriented in the drawings, the dimensions of the outer shell 12 and the inner shell 14 are defined by a diameter measurement and a projection measurement. The diameter measurement is representative of the width of the implant 10a at its widest point and the projection measurement is representative of the height of the implant 10a at its tallest point. In this desirable embodiment, the diameter measurement of the implant 10a is greater than the projection measurement of the implant 10a. Thus, the implant 10a is substantially oval-shaped, elliptical-shaped, or parabolic-shaped. The first alternative embodiment implant 10b and the second alternative embodiment implant 10c are similar in form and function as the implant 10a, except for the differences explicitly discussed herein.

With reference to FIG. 1, the outer shell 12 defines an outer lumen 20 and includes an exterior surface 22 and an interior surface 24. The outer shell 12 may include a valve 26 that bridges a portion between the exterior surface 22 and the interior surface 24 of the outer shell 12. The valve 26 may be placed along various areas of the outer shell 12. The valve 26 allows for filling of the outer lumen 20 of the outer shell 12 with a fluid after the manufacture of the implant 10a, either before or after implantation into a patient. The fluid is preferably a saline solution, yet it is to be understood that the term fluid may refer to both gaseous and liquid fillers or any combination thereof including, but not limited to, electrolyte and organic solutions. The valve 26 also allows for the controlled removal of the fluid without damaging or destroying the implant 10a. Alternatively, the outer lumen 20 may be manufactured as a pre-filled and completely sealed member (not shown), and therefore, not require a valve 26 for the outer lumen 20.

The outer shell 12 is preferably constructed of a non-porous, flexible, biocompatible material, such as silicone elastomer. The outer shell 12 has a wall of sufficient thickness to provide structural integrity to retain fluids while achieving the desired flexibility and malleability of the implant 10a. The outer shell 12 is substantially oval-shaped, with the top of the implant 10a having a convex shape, as oriented in the drawings. Thus, the shape of the implant 10a is defined by the overall external shape of the outer shell 12. In an exemplary embodiment, the enclosed volume within the outer shell 12 is 375 cc. Therefore, the outer shell 12 may accommodate say 375 cc of volume-displacing material, e.g., fluid and fitted shells. It is to be understood that various other volumes of shells 12 may be utilized.

Figure 2:
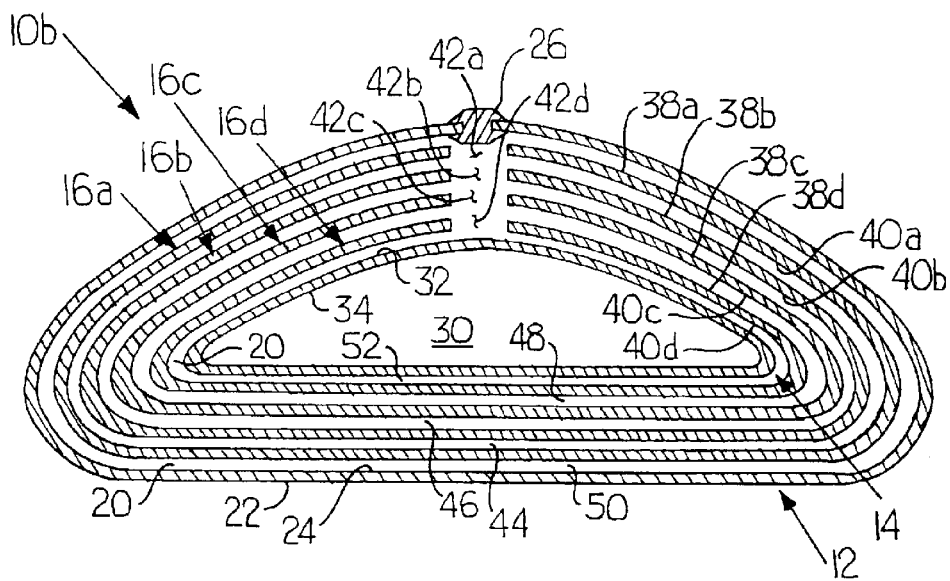
FIG. 2 is a cross-sectional side view of the implant of FIG. 1, according to a first alternative embodiment of the present invention.

The inner shell 14 defines an inner lumen 30, and includes an exterior surface 32 and an interior surface 34. The inner shell 14 is smaller than the outer shell 12 in that the diameter measurement and/or the projection measurement are less than that of the implant 10a. The inner shell 14 is also substantially oval-shaped. In an exemplary embodiment, the enclosed volume of the inner shell 14 is 250 cc. The inner shell 14 is situated within the outer lumen 20 of the outer shell 12, in a relatively central position with respect to interior surface 24 of the outer lumen 20. Similar to the outer shell 12, the inner shell 14 may include a valve 36. The valve 36 bridges the exterior surface 32 and the interior surface 34 of the inner shell 14, as well as the exterior surface 22 and the interior surface 24 of the outer shell 12. The valve 36 allows for filling of the inner lumen 30 of the inner shell 14 with the fluid after the manufacture of the implant 10a, either before or after implantation into a patient. The valve 36 also allows for the controlled removal of fluid without damaging or destroying the implant 10a. Alternatively, as shown in FIG. 2, the inner lumen 30 may be manufactured as a pre-filled and completely sealed member and, therefore, not requiring the valve 36. Thus, the first alternative embodiment implant 10b includes the valve 26 to fill the outer lumen 20, but does not include the valve 36.

Returning to FIG. 1, once implanted, the top of the implant 10a faces away from the chest wall of a patient. Thus, if the implant 10a is not pre-filled, it is desirable to have the valve 26 for the outer lumen 20 and the valve 36 for the inner lumen 30 situated near the top of the implant 10a. This allows the implant 10a to be easily filled after it has been implanted in the patient. Otherwise, if the implant is filled by a surgeon prior to implantation, the valves 26, 36 may be situated along other areas of the exterior surface 22 of the outer shell 12.

One or more fitted shells are situated within the outer lumen 20 of the outer shell 12. It is to be appreciated that there exists an optimal number of fitted shells for effectively achieving the objects of the present invention. The optimal number of shells, which would be apparent to one having ordinary skill in the art, is based upon the characteristics of the implant, e.g., the needs of the patient, the dimensions of the implant, the type of fluid used, etc. Each fitted shell may be formed from a flexible, biocompatible material, such as silicone elastomer, having similar construction in shape as that of the inner shell 14 or the outer shell 12. It is to be understood that the fitted shells may be of varying thicknesses in different areas, relative to each other and relative to the inner shell 14 and the outer shell 12. Desirably, the fitted shells are to be as thin as possible, so as to minimize any bulk within the implant 10*a*. Furthermore, the fitted shells may either be porous or non-porous.

In the desirable embodiment, as depicted in FIG. 1, the implant 10*a* includes four fitted shells: the first fitted shell 16*a*, the second fitted shell 16*b*, the third fitted shell 16*c*, and the fourth fitted shell 16*d*, although it is to be understood that any number of fitted shells may be utilized. Each fitted shell 16*a*–16*d* includes an exterior surface 38*a*–38*d* and an interior surface 40*a*–40*d*, respectively. The primary difference between each fitted shell 16*a*–16*d* and the outer or inner shells 12, 14 is that each fitted shell 16*a*–16*d* has a portion cut out, thereby forming fitted shell openings 42*a*–42*d* in fitted shells 16*a*–16*d*, respectively. The dimensions of each fitted shell are also defined by a diameter measurement and a projection measurement. The diameter measurement is representative of the length of the fitted shell at its widest point and the projection measurement is representative of the height of the fitted shell at its tallest point.

If more than one shell is utilized, as depicted in FIG. 1, then the fitted shells 16*a*–16*d* are contained within each other. Thus, it is preferable that the sizes of the fitted shells 16*a*–16*d* be graduated, in that either the diameter measurement, the projection measurement, or both the diameter and projection measurements of each fitted shell are incrementally larger or smaller than the preceding or successive fitted shells, respectively. For example, in an exemplary embodiment, the unenclosed volume measurements of the fitted shells 16*a*–16*d* are 350 cc, 325 cc, 300 cc, and 275 cc, respectively, with the fitted shells 16*a*–16*d* spaced between 0 cm and 1.0 cm apart from each other. The resultant graduated arrangement occupies the outer lumen 20 of the outer shell 12 with the inner shell 14 enveloped by the fitted shells 16*a*–16*d*. It is to be understood that some of the fitted shells 16*a*–16*d* may be the same size as each other and therefore, not necessarily embody a graduated arrangement. The fitted shell openings 42*a*–42*d* are sized such so as to prevent the inner shell 14 from moving through the fitted shell openings 42*a*–42*d*. Thus, the fourth fitted shell 16*d*, having the smallest volume measurement, is adjacent to the exterior surface 32 of the inner shell 14 and the first fitted shell 16*a*, having the largest volume measurement, is adjacent to the interior surface 24 of the outer shell 12. The second fitted shell 16*b* and the third fitted shell 16*c* are situated between the first fitted shell 16*a* and the fourth fitted shell 16*d* according to their volume measurements. Specifically, the second fitted shell 16*b* is adjacent to the first fitted shell 16*a* and the third fitted shell 16*c* is adjacent to the fourth fitted shell 16*d*. This graduated arrangement creates a space between each of the fitted shells and a space between both the inner and outer shells and the fitted shells. Thus, a space 44 is between the first fitted shell 16*a* and the second fitted shell 16*b*, a space 46 is between the second fitted shell 16*b* and the third fitted shell 11*c*, and a space 48 is between the third fitted shell 16*c* and the fourth fitted shell 16*d*. Similarly, a space 50 is between the outer shell 12 and the first fitted shell 16*a* and a space 52 is between the inner shell 14 and the fourth fitted shell 16*d*.

Insertion of the fluid into the outer lumen 20 of the outer shell 12 causes the fluid to fill the outer lumen 20 and to also envelop the fitted shells 16*a*–16*d* by flowing into the spaces 44, 46, 48, 50, and 52. The shape, size, and graduated arrangement of the fitted shells 16*a*–16*d* result in the fitted shells 16*a*–16*d* maintaining their relative positions within the outer shell 12 and prevent the fitted shells 16*a*–16*d* from wrinkling, folding, or bunching together, which would otherwise be felt as a bulge through the outer shell 12. In conjunction with the inner shell 14 filled with the fluid, this combination provides the implant 10*a* with the simulated static and dynamic characteristics of natural breast tissue. Consequently, a breast reconstructed or enhanced with either the implant 10*a* or the alternative embodiment implant 10*b* will feel like a natural breast and will approximate the movement and feel of the natural breast.

Figure 3:
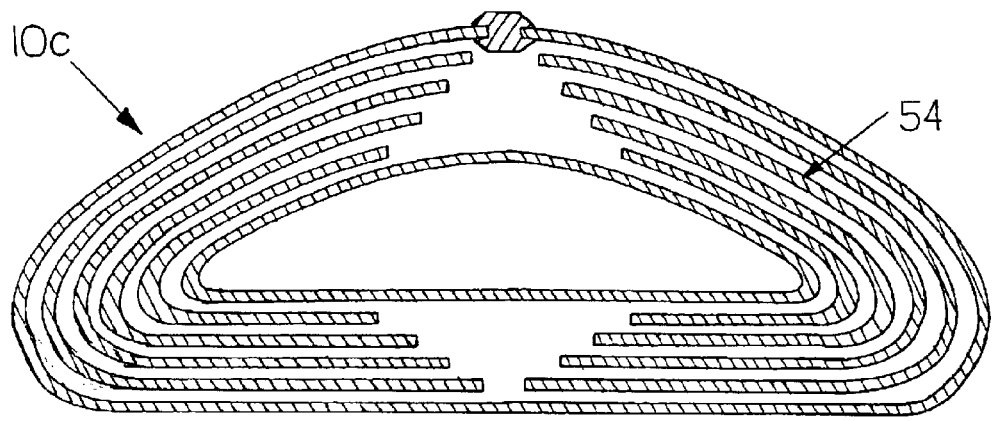
FIG. 3 is a cross-sectional side view of the implant of FIG. 1, according to a second alternative embodiment of the present invention.

With reference to FIG. 3 and with continuing reference to FIGS. 1 and 2, the second alternative embodiment implant 10*c* includes an alternative fitted shell arrangement 54. The alternative fitted shell arrangement 54 performs the same function as the graduated arrangement of the fitted shells 16*a*–16*d* in both the implant 10*a* and the first alternative embodiment implant 10*b*. The difference in the second alternative embodiment implant 10*c* is that the alternative fitted shell arrangement 54 provides more room for the inner shell 14 within the top and bottom of the outer lumen 20. This is accomplished by having graduated diameter fitted shell openings for each fitted shell as well as having fitted shell openings at the bottom of one or more of the fitted shells. It is to be understood that each of the fitted shells may or may not have two graduated diameter fitted shell openings. Furthermore, it is to be understood that the fitted shells in the alternative fitted shell arrangement 54 maintain their relative positions within the outer shell 12, thereby still effectively achieving the objects of the present invention.

Figure 4:
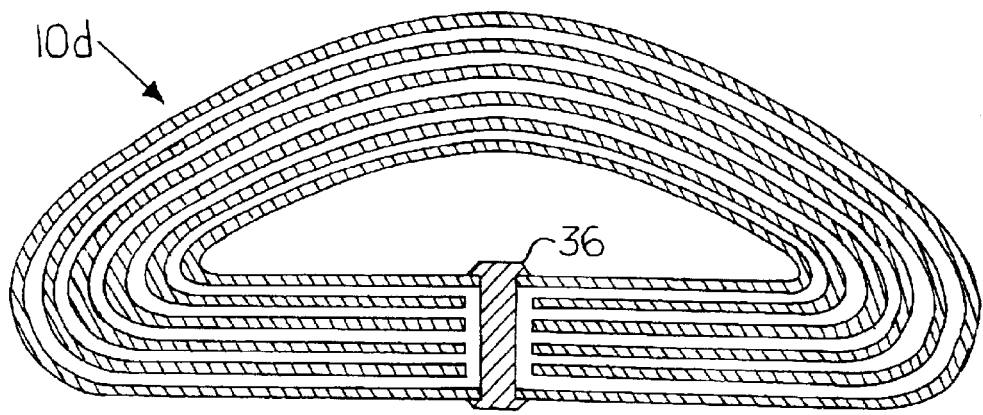
FIG. 4 is a cross-sectional side view of the implant of FIG. 1, according to a third alternative embodiment of the present invention.

With reference to FIG. 4 and with continuing reference to FIG. 1, FIG. 4 serves to illustrate a third alternative embodiment implant 10*d*, wherein the valve 36 is situated at the bottom of the implant 10*d*. The valve 36 of FIG. 4 performs the same function as the valve 36 in the implant 10*a* of FIG. 1, yet is placed in a different area of the implant 10*d*. Still, other embodiments resulting in various placements of valves 26 and 36 may occur to those of ordinary skill in the art.

Figure 5:
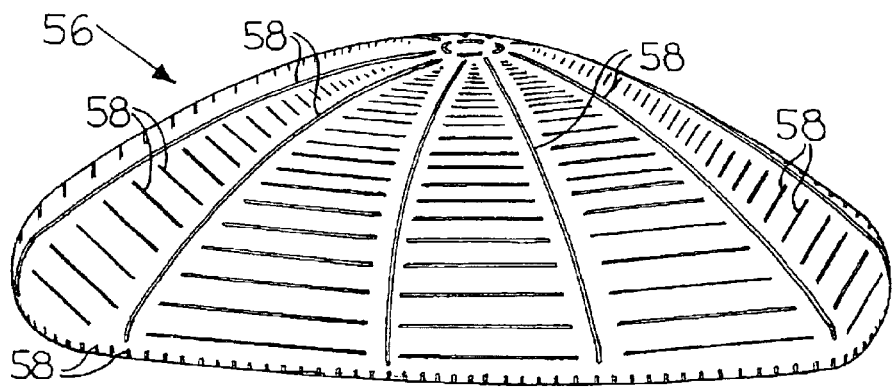
FIG. 5 is a side perspective view of an alternative embodiment fitted shell of the implant of FIG. 1.

With reference to FIG. 5 and with continuing reference to FIG. 1, FIG. 5 depicts a side perspective view of an alternative embodiment fitted shell 56 of the implant 10*a*. Each alternative embodiment fitted shell 56 may have the same shape and construction as the fitted shells 16*a*–16*d*, and may assume a graduated arrangement within the outer lumen 20 of the outer shell 12. Each alternative embodiment fitted shell 56 is different in that the shell 56 includes one or more perforations 58 that allow the fluid to pass through and/or between any other of the alternative embodiment fitted shells 56. Desirably, the perforations 58 are implemented as cut slits circumferentially and outwardly extending from the top to the bottom of the alternative embodiment fitted shell 56 and/or as cut slits radially situated at the edge of the alternative fitted shells 56.

It is to be understood that the implant 10*a* and any other alternative embodiment implants may be of various sizes and configurations. The diameter measurement and the projection measurement of the outer shell 12 and the inner shell 14 may vary in differently sized alternative embodiments. These alternative embodiments may represent various sizes, shapes, or proportions of implants available to the patient. Furthermore, the dimensions of the implant 10*a* may also be different depending on the number of fitted shells and the size of each fitted shell within the implant 10*a*. Additionally, the outer shell 12, the inner shell 14, both the outer shell 12 and the inner shell 14, or neither the outer shell 12 nor the inner shell 14 may be pre-filled with the fluid by a manufacturer of the implant 10a. Thus, shells that are not pre-filled require the valve to be incorporated therein.

The above invention has been described with reference to the preferred and alternative embodiments. Obvious modifications, combinations, and alterations will occur to others upon reading the preceding detailed description. It is intended that the invention be construed as including all such modifications, combinations, and alterations insofar as they come within the scope of the appended claims or the equivalents thereof.

What is claimed is:

1. A surgically implantable prosthetic device, comprising:
   a first enclosing shell having an exterior surface, an interior surface, and enclosing a lumen, wherein the lumen enclosed by the first shell is able to accommodate a first fluid therein;
   a second enclosing shell having an exterior surface, an interior surface, and enclosing a lumen, wherein the lumen enclosed by the second shell is able to accommodate a second fluid therein; and
   one or more non-enclosing fitted shells situated between the exterior surface of the second shell and the interior surface of the first shell such that all surfaces of the fitted shells are in communication with the first fluid.

2. The prosthetic device of claim 1, wherein the one or more fitted shells are adjacent to each other.

3. The prosthetic device of claim 2, wherein the one or more fitted shells comprise an innermost fitted shell and an outermost fitted shell, wherein the innermost fitted shell is adjacent to the exterior surface of the second shell and the outermost fitted shell is adjacent to the interior surface of the first shell.

4. The prosthetic device of claim 2, wherein each fitted shell is generally dome-shaped and has a diameter measurement and a projection measurement, and the projection measurement increases as the diameter measurement increases.

5. The prosthetic device of claim 4, wherein the diameter measurement of one of the fitted shells is greater than the diameter measurement of any other fitted shell.

6. The prosthetic device of claim 5, wherein the fitted shells are arranged in a graduated manner based upon the diameter measurement of each fitted shell, wherein the fitted shell having the smallest diameter measurement is adjacent to the exterior surface of the second shell and wherein the fitted shell having the largest diameter is adjacent to the interior surface of the first shell.

7. The prosthetic device of claim 1, wherein the one or more fitted shells include at least one or more holes.

8. The prosthetic device of claim 1, wherein the one or more fitted shells include at least one perforation.

9. The prosthetic device of claim 1, wherein at least one of the first shell, the second shell, and the fitted shells are constructed of a biocompatible material.

10. The prosthetic device of claim 1, wherein at least one of the first shell and the second shell are constructed of a nonporous material.

11. The prosthetic device of claim 1, wherein the distance between each of the one or more fitted shells is between 0 cm and 1.0 cm.

12. The prosthetic device of claim 1, wherein the lumen enclosed by the first shell is filled with the first fluid.

13. The prosthetic device of claim 12, wherein the first shell includes a first valve for allowing for the filling of the lumen enclosed by the first shell with the first fluid.

14. The prosthetic device of claim 1, wherein the lumen enclosed by the second shell is filled with the second fluid.

15. The prosthetic device of claim 14, wherein the second shell includes a second valve for allowing for the filling of the lumen enclosed by the second shell with the second fluid.

16. The prosthetic device of claim 1, wherein the first fluid is able to envelop at least the one or more fitted shells.

17. The prosthetic device of claim 1, wherein the first fluid and the second fluid are at least one of an organic solution and a synthetic solution.

18. The prosthetic device of claim 1, wherein the first fluid and the second fluid are at least one of an electrolyte solution and a saline solution.

19. The prosthetic device of claim 18, wherein at least one of the first fluid and the second fluid further comprises a lubricating agent.

20. The prosthetic device of claim 1, wherein the device is a breast implant.

* * * * *